(12) United States Patent
Asgharian

(10) Patent No.: US 7,169,767 B2
(45) Date of Patent: *Jan. 30, 2007

(54) OPHTHALMIC COMPOSITIONS CONTAINING GALACTOMANNAN POLYMERS AND BORATE

(75) Inventor: Bahram Asgharian, Arlington, TX (US)

(73) Assignee: Alcon Manufacturing, Ltd., Forth Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/997,643

(22) Filed: Nov. 24, 2004

(65) Prior Publication Data

US 2005/0075313 A1    Apr. 7, 2005

Related U.S. Application Data

(63) Continuation of application No. 10/437,570, filed on May 14, 2003, now Pat. No. 6,838,449, which is a continuation of application No. 10/128,559, filed on Apr. 22, 2002, now Pat. No. 6,583,124, which is a continuation of application No. 09/423,762, filed as application No. PCT/US98/14596 on Jul. 17, 1998, now Pat. No. 6,403,609.

(60) Provisional application No. 60/054,132, filed on Jul. 29, 1997.

(51) Int. Cl.
*A61K 33/22* (2006.01)
*A61K 31/736* (2006.01)

(52) U.S. Cl. ............... 514/54; 514/310; 514/839; 514/912; 514/944; 536/123.1; 536/124; 536/128; 424/401; 424/402; 424/427; 424/659; 507/209; 507/241; 507/271; 166/300; 166/308.5

(58) Field of Classification Search .................. 514/54, 514/310, 839, 912, 944; 536/123.1, 124, 536/128; 424/401, 402, 427, 659, 660; 507/209, 507/241, 271; 166/300, 308.5
See application file for complete search history.

(56) References Cited

U.S. PATENT DOCUMENTS

| | | |
|---|---|---|
| 3,843,782 A | 10/1974 | Krezanoski et al. |
| 4,136,173 A | 1/1979 | Pramoda et al. |
| 4,136,177 A | 1/1979 | Lin et al. |
| 4,136,178 A | 1/1979 | Lin et al. |
| 4,255,415 A | 3/1981 | Chrai et al. |
| 4,323,467 A | 4/1982 | Fu |

(Continued)

FOREIGN PATENT DOCUMENTS

EP    0 386 960 A2    9/1990

(Continued)

OTHER PUBLICATIONS

*Ophthalmic Drug Facts '99*, Facts and Comparisons, Ch. 3, St. Louis, MO, pp. 25-39 (1999).

(Continued)

*Primary Examiner*—Shaojia Anna Jiang
*Assistant Examiner*—Devesh Khare
(74) *Attorney, Agent, or Firm*—Gregg C. Brown

(57) ABSTRACT

The present invention is directed to ophthalmic compositions containing a gelling amount of a combination of galactomannan polysaccharides and borates. The compositions gel or partially gel upon administration to the eye. The present invention also discloses methods of topical ophthalmic administration of the compositions to the eye.

4 Claims, 3 Drawing Sheets

U.S. PATENT DOCUMENTS

| Patent No. | Kind | Date | Inventor | Ref |
|---|---|---|---|---|
| 4,370,325 | A | 1/1983 | Packman | |
| 4,436,730 | A | 3/1984 | Ellis et al. | |
| 4,474,751 | A | 10/1984 | Haslam et al. | |
| 4,500,441 | A | 2/1985 | Tanaka et al. | |
| 4,861,760 | A | 8/1989 | Mazuel et al. | |
| 5,077,033 | A | 12/1991 | Viegas et al. | |
| 5,082,579 | A | 1/1992 | Dawson | |
| 5,126,141 | A | 6/1992 | Henry | |
| 5,145,590 | A | 9/1992 | Dawson | |
| 5,160,643 | A | 11/1992 | Dawson | |
| 5,188,826 | A | 2/1993 | Chandrasekaran et al. | |
| 5,192,535 | A | 3/1993 | Davis et al. | |
| 5,318,780 | A | 6/1994 | Viegas et al. | |
| 5,346,703 | A | 9/1994 | Viegas et al. | |
| 5,372,732 | A | 12/1994 | Harris et al. | |
| 5,376,693 | A | 12/1994 | Viegas et al. | |
| 5,457,093 | A | 10/1995 | Cini et al. | |
| 5,607,698 | A | 3/1997 | Martin et al. | |
| 5,653,972 | A | 8/1997 | Desai et al. | |
| 5,773,025 | A | 6/1998 | Baichwal | |
| 5,919,742 | A | 7/1999 | Tsuzui et al. | |
| 5,922,340 | A | 7/1999 | Berde et al. | |
| 5,972,326 | A | 10/1999 | Galin et al. | |
| 6,056,950 | A | 5/2000 | Saettone et al. | |
| 6,316,506 | B2 | 11/2001 | Asgharian | |
| 6,403,609 | B1 * | 6/2002 | Asgharian | 514/310 |
| 6,486,138 | B1 * | 11/2002 | Asgharian et al. | 514/54 |
| 6,495,608 | B1 * | 12/2002 | Asgharian | 424/659 |
| 6,583,124 | B2 * | 6/2003 | Asgharian | 514/54 |
| 6,838,449 | B2 * | 1/2005 | Asgharian | 514/54 |
| 2005/0129771 | A1 * | 6/2005 | Asgharian | 424/488 |

FOREIGN PATENT DOCUMENTS

| | | |
|---|---|---|
| JP | 6-345653 | 12/1994 |
| JP | 10221654 | 8/1998 |
| WO | WO 94/10976 | 5/1994 |
| WO | WO 97/30092 | 8/1997 |

OTHER PUBLICATIONS

Albasini, et al.; "Evaluation of Polysaccharides Intended for Ophthalmic Use in Ocular Dosage Forms", *Il Farmaco*, vol. 50 (9), pp. 633-642, (1995).

Power, et al., "Gel Transition Studies on Non-ideal Polymer Networks Using Small Amplitude Oscillatory Rheometry", *Journal of Rheology*, vol. 42 (5), pp. 6-22, (1998).

*The Merck Index;* Twelfth Edition, 1996, p. 1548.

Bello, et al. "Effect of Intermolecular Cross Links on Drag Reduction by Polymer Solutions", *Polymer Bulletin*, vol. 36, pp. 111-118 (1996).

Kesavan, et al., "Rheology of Guar and HPG Cross-Linked by Borate", *Macromolecules*, vol. 25, pp. 2026-2032, (1992).

\* cited by examiner

OPHTHALMIC COMPOSITIONS CONTAINING GALACTOMANNAN POLYMERS AND BORATE

CROSS-REFERENCE TO RELATED APPLICATIONS

The present application is a continuation of U.S. patent application Ser. No. 10/437,570 filed May 14, 2003 (U.S. Pat. No. 6,838,449), which is a continuation of U.S. patent application Ser. No. 10/128,559 filed Apr. 22, 2002 (U.S. Pat. No. 6,583,124), which is a continuation of U.S. patent application Ser. No. 09/423,762 filed Nov. 12, 1999 (U.S. Pat. No. 6,403,609), which is the National Stage of International Application No. PCT/US98/14596 filed Jul. 17, 1998, which claims benefit of U.S. Provisional Application Ser. No. 60/054,132 filed Jul. 29, 1997.

BACKGROUND OF THE INVENTION

The present invention relates to the use of adjuvants in topical ophthalmic compositions. In particular, the present invention relates to pharmaceutical compositions comprising galactomannan polymers in combination with borates, and methods for the controlled administration of pharmaceutically active agents to patients, wherein the compositions are administered as liquids which thicken to form gels upon instillation into the eye. The transition from liquid to gel is primarily due to the change in pH and ionic strength.

Topical ophthalmic compositions have taken the form of liquids, ointments, gels and inserts. Liquid compositions for drop-wise instillation of pharmaceutically active agents to the eye provide for easy administration, but they do not always provide for an accurate dosage amount, as portions of the liquid are often blinked away during administration or drained down the punctum into the nasal passage. Ointments and gels, which usually reside in the eye longer than a liquid and therefore provide for more accurate administration, often interfere with a patient's vision. Ocular inserts, both bioerodible and non-bioerodible, are also available and allow for less frequent administration of drug. These inserts, however, require complex and detailed preparation and are frequently uncomfortable to the wearer. An additional problem with non-bioerodible inserts is that they must be removed after use.

U.S. Pat. No. 4,136,173 (Pramoda, et al.) disclose the use of therapeutic compositions containing xanthan gum and locust bean gum which are administered in liquid form and gel upon instillation. This reference describes a mechanism for transition from liquid to gel involving pH change. pH sensitive gels such as carbomers, xanthan, gellan, and those described above, need to be formulated at or below the pKa of their acidic groups (typically at a pH of about 2 to 5). Compositions formulated at low pH, however, are irritating to the eye.

The use of locust bean gum to form a gel vehicle for ophthalmic drug delivery is described in U.S. Pat. No. 4,136.177 (Lin, et al.). However, the gels described by Lin, et al. are formed at the time of manufacture, rather than upon application to the eye.

U.S. Pat. No. 4,861,760 (Mazuel, et al.) discloses ophthalmic compositions containing gellan gum which are administered to the eye as non-gelled liquids and gel upon instillation due to a change in ionic strength. These systems do not involve the use of small cross-linking molecules, but instead provide gel characteristics due to self cross-linking during ionic condition changes.

Gels involving the cross-linking of polysaccharides with borates are disclosed for use as well fracturing fluids in U.S. Pat. No. 5,082,579 (Dawson), U.S. Pat. No. 5,144,590 (Dawson), and U.S. Pat. No. 5,160,643 (Dawson). These patents describe the use of borates and polysaccharides for industrial oil well excavation.

The ophthalmic use of current gelling liquid systems have a number of drawbacks. For example, natural polymers such as xanthan gum have the disadvantage of lot to lot variability due to variations in source and/or limited manufacturing controls during processing. These variabilities cause significant undesirable changes in the properties of the compound, such as variable gelling characteristics. Thermogelling systems such as polyethylene oxide/polypropylene oxide block copolymers ("PEO/PPO") lose water in order to form gels, and consequently result in turbid gels. Polyvinyl alcohol ("PVA")-borate combination gelling systems need to be formulated at low pH, and therefore, can cause ocular irritation upon instillation. Other gelling systems have viscosity, rehydration and cloud point instability problems associated with autoclaving.

Polyvinyl alcohol crosslinking with borates have been disclosed in U.S. Pat. No. 4,255,415 (Sukhbir et al.). These compositions are pre-formed gels, and are therefore hard to dispense. WIPO Publication No. WO 94/10976 (Goldenberg et al.) discloses a low pH PVA-borate delivery system that does go through liquid/gel transition. This system has the disadvantage, however, of limited gelling effects, and only at certain concentrations of PVA depending on the molecular weight of the PVA utilized. Furthermore, since the crosslinking cites are unlimited with this system, strong local gelation upon addition of base has limited its manufacturing, and therefore, polyvinyl pyrrolidone presumably has been included in these compositions to overcome the shortcoming. The novel gelling system of the present invention does not have the above limitation.

SUMMARY OF THE INVENTION

The present invention is directed to topical ophthalmic compositions comprising galactomannan polymers and borate compounds which provide controlled administration of a drug to the eye. The invention is based on a new gelling system which comprises a galactomannan polysaccharide and a borate crosslinker which forms a gel upon increases in pH and ionic strength. In this novel system, bisdiol borates crosslink with the cis diol groups of the sugar moieties of the polysaccharide. The compositions are administered as liquids or partially gelled liquids (hereinafter "liquids") which thicken to form gels upon instillation into the eye. Alternatively, the compositions may not contain a pharmaceutically active agent, and can be administered to the eye for lubrication or to supplement tears in the treatment of, for example, dry eye.

The present invention galactomannan-borate gelling system has several advantages over other gelling systems. One advantage is that the compositions of the present invention are clear solutions and the resultant gel is also crystal clear. While other systems may become opaque or cloudy upon instillation, the crystal clear gel of the present invention provides greater clarity of vision to the treated eye. The present invention compositions may be formulated at slightly acidic to neutral pH and require only a minor pH change to activate gelation (i.e., about 0.5 to 1.0 pH unit).

This feature minimizes possible irritation of the eye resulting from acidic exposure, such as may result with other pH sensitive systems which require a pH change of about 2.4 to about 4.4 pH units (i.e., are formulated with a pH of about 3–5). Galactomannan polymers are also heat stable and show no cloud point even during autoclaving conditions. As such, viscosity and rehydration problems resulting from batch scale up, such as exist with PVA and carbomer polymer systems, are not present with the galactomannan polymer containing compositions of the present invention.

Galactomannan polysaccharides are non-ionic and, in combination with borates at acidic to neutral pH, are also essentially non-ionic. Thus, the polymer system is completely compatible with anionic, neutral and cationic drugs. Furthermore, the preservative efficacy of the preservatives are not compromised by the presence of the polymer. Typically, the efficacy of benzalkonium chloride or other cationic preservatives are compromised with anionic polymers such as gellan and carageenan, and excess preservative may therefore be needed in those systems. Increases in preservative concentration may also increase irritation and toxicity of the composition.

The galactomannan-borate gelling system of the present invention has other advantages. Galactomannan polymers have a relatively low molecular weight and are therefore easy to manufacture and scale up. Galactomannan polymers are also readily available and have been used in food and personal care products such that the polymers are considered to be safe. Furthermore, control or manipulation of the gelling characteristics of the galactomannan-borate gelling compositions of the present invention is relatively simple as compared with prior art systems. The gelling properties of other single polymer systems, such as ionomers, e.g., gellan and carageenans, and thermogels, e.g., poloxamines and poloxamers, are typically related to the molecular weight and the number of functional groups of the polymers. Thus, in order to change the gel point or degree of gelation of those prior art systems, one would need to modify the base polymer—a labor intensive activity. In contrast, by simply manipulating the borate to galactomannan ratio in the present invention compositions, a wide range of gelling characteristics is available in order to fine tune the compositions to the targeted requirements (see FIGS. 1 and 2). Moreover, as illustrated in FIG. 3, the galactomannans of the present invention (e.g., guar gum) demonstrate excellent gelling consistency and reproducibility, though the type or source of the galactomannan is varied.

Still other advantages are present in the compositions of the present invention. The galactomannan polymer and the borate crosslinker compositions of the present invention are liquids and, therefore, easy to dispense. Some gelling systems such as gellan gum, as disclosed in U.S. Pat. No. 4,861,760 (Mazuel et al.), are thixotropic, which may require shaking to increase the fluidity and ease of dispensing. The present invention compositions contain a relatively low concentration of galactomannan (about 0.2 to 0.5%) as compared to some thermogelling systems such as PEO/PPO block copolymers, which require very high concentrations. Lower concentrations of the gelling polymer provide lower potential toxicity and ease of preservation from microbial contamination over higher concentration systems.

The methods of the present invention involve the topical administration of the galactomannan-borate containing compositions of the present invention.

The present invention is also directed to methods of sterilization of the galactomannans involving autoclaving.

DETAILED DESCRIPTION OF THE INVENTION

The present invention is directed to ophthalmic compositions which comprise one or more galactomannan polysaccharide(s) and one or more borate compound(s). The present invention is also directed to methods of using these compositions to treat various ophthalmic disorders including dry eye, glaucoma, ocular hypertension, infection, allergy and inflammation.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1–4)-β-D-mannopyranosyl units with α-D-galactopyranosyl units attached by (1–6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1–C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired.

The borate compounds which may be used in the compositions of the present invention are boric acid and other pharmaceutically acceptable salts such as sodium borate (borax) and potassium borate. As used herein, the term "borate" refers to all pharmaceutically suitable forms of borates. Borates are common excipients in ophthalmic formulations due to good buffering capacity at physiological pH and well known safety and compatibility with a wide range of drugs and preservatives. Borates also have inherent bacteriostatic and fungistatic properties, and therefore aid in the preservation of the compositions.

Figure 1:
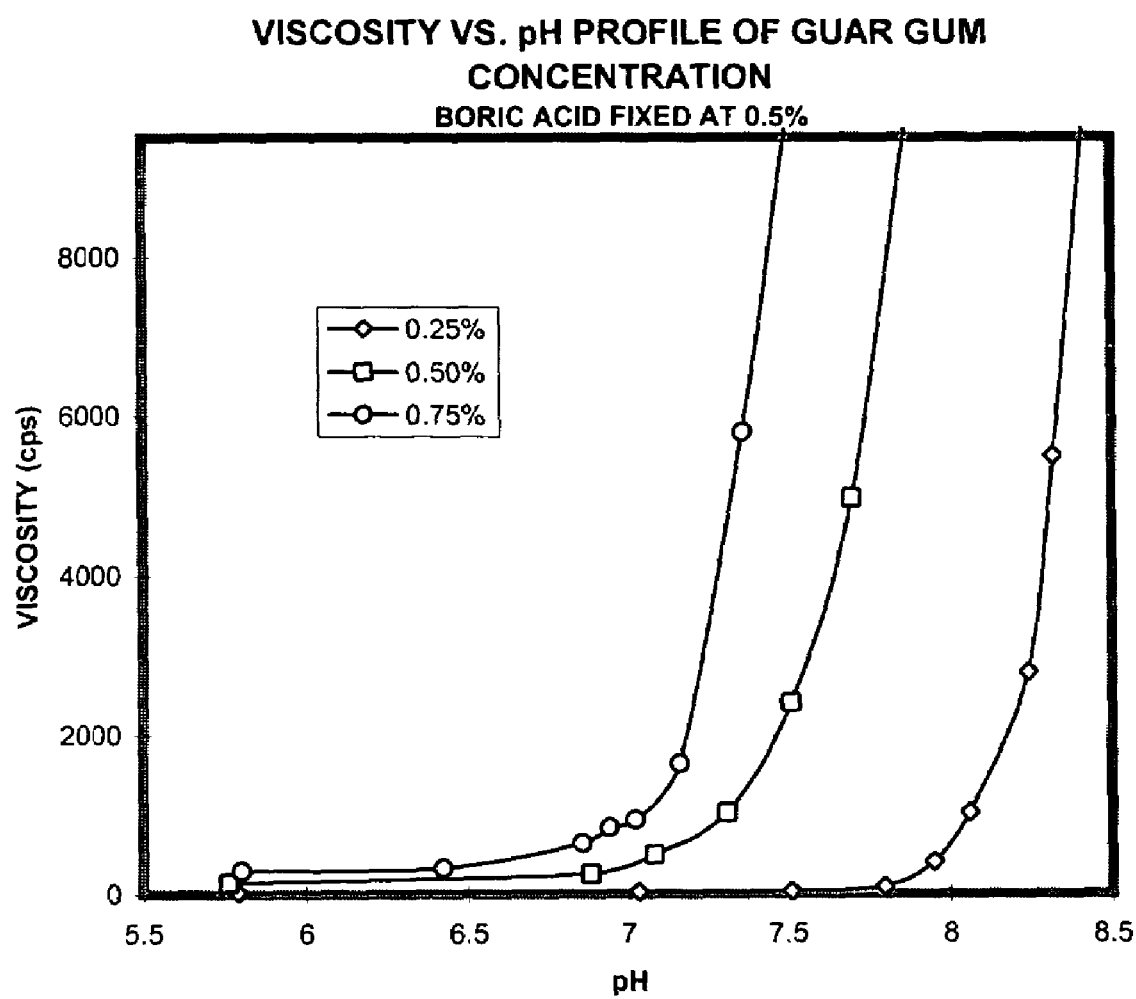
FIG. 1 is a graph illustrating the gelling characteristics of various concentrations of guar gum in the presence of borate, relative to pH.
Figure 2:
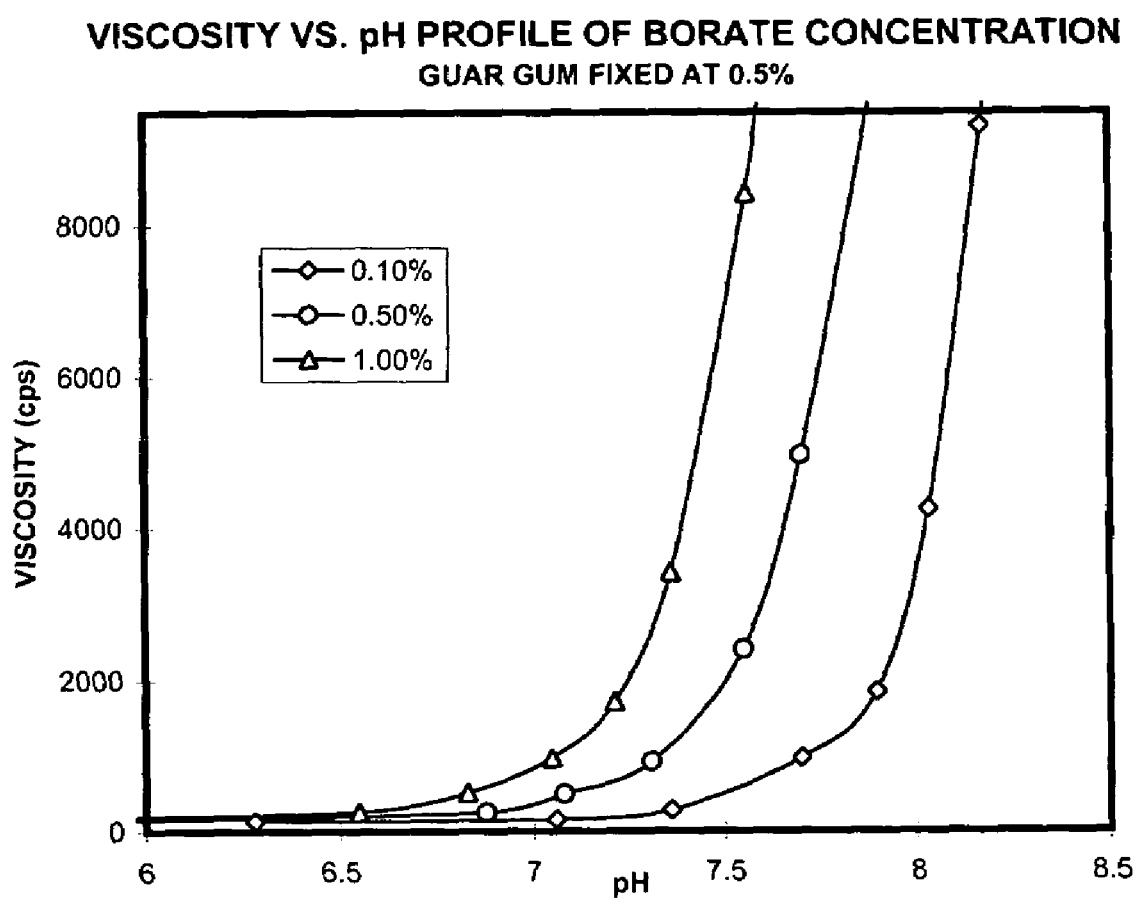
FIG. 2 is a graph illustrating the gelling characteristics of various concentrations of borate in the presence of guar gum, relative to pH.
Figure 3:
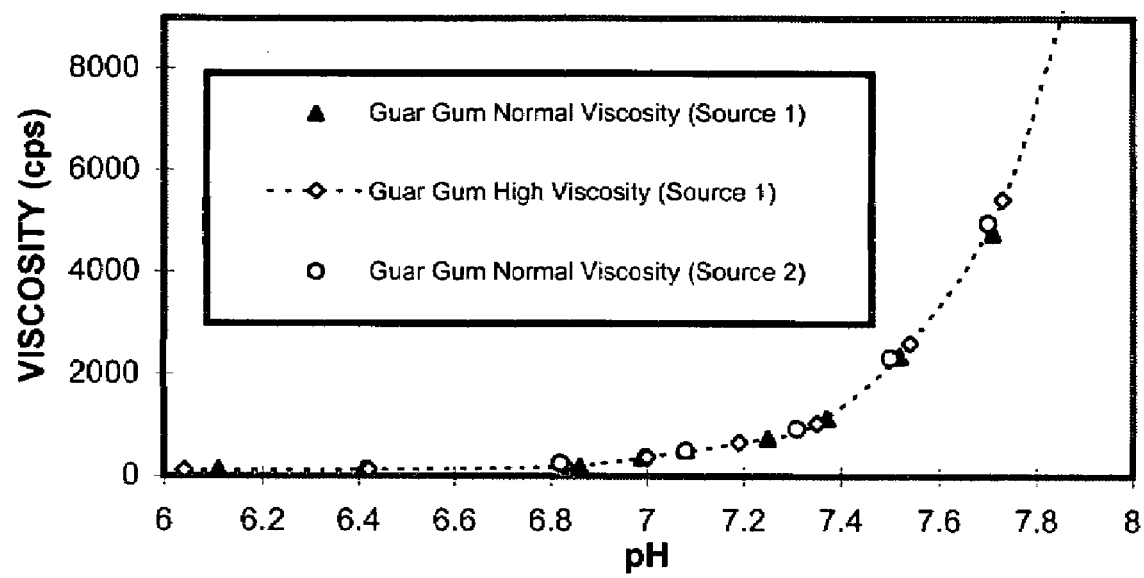
FIG. 3 is a graph illustrating the uniformity of the gelling characteristics of three different types/sources of guar gum.

The present invention compositions comprise one or more galactomannan(s) in the amount of from about 0.1 to 5% weight/volume ("w/v") and borate in the amount of from about 0.05 to 5% (w/v). Preferably, the compositions will contain 0.2 to 2.0% (w/v) of galactomannan and 0.1 to 2.0% (w/v) of a borate compound. Most preferably, the compositions will contain 0.3 to 0.8% (w/v) of galactomannan and 0.25 to 1.0% (w/v) of a borate compound. The particular amounts will vary, depending on the particular gelling properties desired. In general, the borate or galactomannan concentration may be manipulated in order to arrive at the appropriate viscosity of the composition upon gel activation (i.e., after administration). As shown in FIGS. 1 and 2, manipulating either the borate or galactomannan concentration provides stronger or weaker gelation at a given pH. If a strongly gelling composition is desired, then the borate or galactomannan concentration may be increased. If a weaker gelling composition is desired, such as a partially gelling composition, then the borate or galactomannan concentration may be reduced. Other factors may influence the gelling features of the compositions of the present invention, such as the nature and concentration of additional ingredients in the compositions, such as salts, preservatives, chelating agents and so on. Generally, preferred non-gelled compositions of the present invention, i.e., compositions not yet gel-activated by the eye, will have a viscosity of from about 5 to 1000 cps. Generally, preferred gelled compositions of the present invention, i.e., compositions gel-activated by the eye, will have a viscosity of from about 50 to 50,000 cps.

The galactomannans of the present invention may be obtained from numerous sources. Such sources include guar gum, locust bean gum and tara gum, as further described below. Additionally, the galactomannans may also be obtained by classical synthetic routes or may be obtained by chemical modification of naturally occurring galactomannans.

Guar gum is the ground endosperm of *Cyamopisis tetragonolobus* (L.) Taub. The water soluble fraction (85%) is called "guaran" (molecular weight of 220,000), which consists of linear chains of (1–4)-β-D mannopyranosyl units with α-D-galactopyranosyl units attached by (1–6) linkages. The ratio of D-galactose to D-mannose in guaran is about 1:2. The gum has been cultivated in Asia for centuries and is primarily used in food and personal care products for its thickening property. It has five to eight times the thickening power of starch. Its derivatives, such as those containing hydroxypropyl or hydroxypropyltrimonium chloride substitutions, have been commercially available for over a decade. Guar gum may be obtained, for example, from Rhone-Polulenc (Cranbury, N.J.), Hercules, Inc. (Wilmington, Del.) and TIC Gum, Inc. (Belcamp, Md.).

Locust bean gum or carob bean gum is the refined endosperm of the seed of the carob tree, *ceratonia siliqua*. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the United States commercially, but the gum may be obtained from various sources outside the United States.

In order to limit the extent of cross-linking to provide a softer gel characteristic, chemically modified galactomannans such as hydroxypropyl guar may be utilized. Modified galactomannans of various degree of substitution are commercially available from Rhone-Poulenc (Cranbury, N.J.). Hydroxypropyl guar with low molar substitution (e.g., less than 0.6) is particularly preferred.

Other ingredients may be added to the compositions of the present invention. Such ingredients generally include tonicity adjusting agents, chelating agents, active pharmaceutical agent(s), solubilizers, preservatives, pH adjusting agents and carriers. Other polymer or monomeric agents such as polyethylene glycol and glycerol may also be added for special processing. Tonicity agents useful in the compositions of the present invention may include salts such as sodium chloride, potassium chloride and calcium chloride; non-ionic tonicity agents may include propylene glycol and glycerol; chelating agents may include EDTA and its salts; solubilizing agents may include Cremophor EL® and tween 80; other carriers may include amberlite® IRP-69; pH adjusting agents may include hydrochloric acid, Tris, triethanolamine and sodium hydroxide; and suitable preservatives may include benzalkonium chloride, polyquaternium-1 and polyhexamethylene biguanide. The above listing of examples is given for illustrative purposes and is not intended to be exhaustive. Examples of other agents useful for the foregoing purposes are well known in ophthalmic formulation and are contemplated by the present invention.

Combination of the gelling system of the present invention with prior art gelling systems is also contemplated by the present invention. Such systems may include the inclusion of ionomers, such as xanthan, gellan, carageenan and carbomers, and thermogels, such as ethylhydroxyethyl cellulose.

In general, the compositions of the present invention will be used to administer various pharmaceutically active compounds to the eye. Such pharmaceuticals may include, but are not limited to, anti-hypertensive, anti-glaucoma, neuroprotective, anti-allergy, muco-secretagogue, angiostatic, anti-microbial, pain relieving and anti-inflammatory agents.

Examples of pharmaceutically active agents which may be included in the compositions of the present invention, and administered via the methods of the present invention include, but are not limited to: glaucoma agents, such as betaxolol, timolol, pilocarpine, carbonic anhydrase inhibitors and prostglandins; dopaminergic antagonists; post-surgical antihypertensive agents, such as para-amino clonidine (apraclonidine); anti-infectives, such as ciprofloxacin and tobramycin; non-steroidal and steroidal anti-inflammatories, such as naproxen, diclofenac, suprofen, ketorolac, tetrahydrocortisol and dexamethasone; proteins; growth factors, such as epidermal growth factor; and anti-allergics.

Optionally, the compositions of the present invention may be formulated without a pharmaceutically active compound. Such compositions may be used to lubricate the eye or provide artificial tear solutions to treat, for example, dry eye. In general, artificial tear solutions will contain tonicity agents, polymers and preservatives, as described above. The amount of galactomannan and borate contained in the artificial tear solutions will vary, as described above, but will generally be in the amount of from 0.1 to 3.0% (w/v) and 0.1 to 2.0% (w/v), respectively.

In general, the compositions of the present invention are formulated in two parts. The galactomannan polymer is hydrated and sterilized (Part I). Any pharmaceutical agent(s) and/or other ingredients to be included in the composition are then dissolved in water and sterile filtered (Part II). Parts I and II are then combined and the pH of the resultant mixture is adjusted to the target level, generally 6.0 to 7.0. If the pharmaceutical agent(s) to be included have low water solubility, they will generally be added last. In certain cases, it may be preferred to sterilize the pharmaceutical agent(s) separately, and then aseptically add the agent(s) and other ingredients together.

Sterilization of the galactomannan polysaccharide can be accomplished by autoclaving. Since the polymers undergo depolymerization at the extreme conditions of autoclaving, non-aqueous autoclaving is generally preferred. This can be accomplished by dispersing the polymer in a suitable organic liquid such as low molecular weight polyethylene glycols. The resulting suspension may then be autoclaved to sterilize the polymer. The sterilized polymer is then hydrated aseptically, prior to admixture with the other ingredients.

The following example illustrates a novel method of sterilizing a galactomannan polysaccharide of the present invention:

EXAMPLE 1

Preliminarily, a compounding vessel (20 L stainless steel pressure can), a 0.2 micron sterilizing filter, a receiving vessel (20 L carboy), a 4.5 micron polishing filter, a 0.2 micron sterilizing filter, a vent filter, and the filling equipment are sterilized by autoclaving.

In a beaker equipped with an overhead agitator, add the weighed amount of polyethylene glycol 400 (200 g). While mixing slowly disperse the weighed amount of hydroxypropyl ("HP")Guar gum (100 g). Mix until completely homogeneous. In a 500 ml Schott bottle, equipped with a magnetic stir bar, weigh exactly 120.0 g of the HPGuar gum/PEG-400 dispersion. Prepare to sterilize by autoclaving. In a second identical 500 ml Schott bottle weigh exactly 120.0 g of the same dispersion. Prepare to use as a dummy during the autoclaving cycle. To both bottles add 1.3 ml of purified water (amount equivalent, by volume, of the microorganism suspension used to inoculate the bottles during the validation study). Mix both bottles for 10 minutes using a magnetic stir plate. Autoclave the HPGuar gum/PEG-400 dispersion using the validated time-temperature cycle of 80 minutes at 125° C.

The other set of ingredients to be included in the final formulation may be prepared separately by various methods known in the art. The resultant mixture can be added by sterile filtration to the compounding vessel, along with the HPGuar gum/PEG-400 preparation.

Aseptically transfer the sterilized HPGuar gum/PEG-400 dispersion into the pre-sterilized compounding vessel. Rinse the bottle content with sterilized purified water. Bring the content of the compounding vessel to exactly 95% of the theoretical batch weight (19.0 liters or 19.06 Kg) using sterile room temperature purified water. Allow the HPGuar gum/PEG slurry to hydrate while mixing, at moderate speed, in the compounding vessel for a minimum of 2 hours. Transfer the contents of the compounding vessel through a 4.5 micron pre-sterilized polishing filter into the pre-sterilized receiving vessel equipped with a stir bar. There will be some loss of the contents due to the product held in filter housing and filter cartridge. (If a pressure can is used as compounding vessel, the recommended pressure for clarification filtration is approximately 30 psi.) Check and adjust pH, if necessary, to 6.9–7.1 (target 7.0) using 1N NaOH or 1N HCl. Approximately 3–4 ml of 1N NaOH per 1 liter of final batch weight is needed to achieve the desired pH. QS to final batch weight using sterile purified water. Mix at low speed for a minimum of 30 minutes.

The following examples further illustrate preferred ophthalmic compositions of the present invention:

EXAMPLE 2

The following is an example of a topical ophthalmic composition containing timolol.

| Compound | Amount % (w/v) |
| --- | --- |
| Timolol Maleate | 0.68* |
| Boric Acid | 0.5 |
| Guar Gum | 0.5 |
| PEG-400 | 1.0 |
| Sodium Chloride | 0.5 |
| Benzalkonium Chloride | 0.01 |
| Sodium Hydroxide/Hydrochloric Acid | QS to pH 6.5 |
| Purified Water | QS |

*0.68% Timolol Maleate is equivalent to 0.5% Timolol.

The above formulation is prepared by first preparing a Part I and Part II mixture. The guar gum is first dispersed in PEG-400 and autoclaved as Part I. The other ingredients are dissolved in about 90% of the volume of water and sterile filtered in a receiving vessel as Part II. Part I is then added to Part II aseptically. The pH may then be adjusted aseptically and the batch is then brought to final weight (volume). The combined solution is then passed through a 1.0 μm polish filter, aseptically, to remove the particulates.

EXAMPLE 3

The following is another example of a topical ophthalmic composition containing timolol.

| Compound | Amount % (w/v) |
| --- | --- |
| Timolol Maleate | 0.34* |
| Boric Acid | 0.5 |
| Guar Gum | 0.25 |
| Glycerol | 1.0 |
| Benzalkonium Chloride | 0.005 |
| Sodium Hydroxide/Hydrochloric Acid | QS to pH 7.0 |
| Purified Water | QS |

*0.34% Timolol Maleate is equivalent to 0.25% Timolol.

The above composition may be prepared in a similar way as the Example 2 composition.

EXAMPLE 4

The following is an example of an artificial tear solution.

| Compound | Amount % (w/v) |
| --- | --- |
| Boric Acid | 0.5 |
| Hydroxpropyl Guar | 0.3 |
| Propylene glycol | 1.4 |
| Polyquaternium-1 | 0.0005 |
| Sodium Hydroxide/Hydrochloric Acid | QS to pH 6.8 |
| Purified Water | QS |

The above composition may be prepared in a similar way as the Example 2 composition.

The invention in its broader aspects is not limited to the specific details shown and described above. Departures may be made from such details within the scope of the accompanying claims without departing from the principles of the invention and without sacrificing its advantages.

What is claimed is:

1. A method of delivering a pharmaceutical agent to the eye which comprises topically administering to the eye a sterile ophthalmic composition comprising:
- a therapeutically effective amount of a pharmaceutically active agent selected from the group consisting of steroidal anti-inflammatory agents, non-steroidal anti-inflammatory agents and combinations thereof;
- 0.1 to 5% (w/v) of a galactomannan selected from the group consisting of guar, hp guar and combinations thereof;
- 0.05 to 5% (w/v) of a borate compound; and
- water.

2. The method of claim 1, wherein the galactomannan comprises hp-guar.

3. The method of claim 1, wherein the pharmaceutically active agent comprises a steroidal anti-inflammatory agent.

4. The method of claim 1, wherein the pharmaceutically active agent comprises a non-steroidal anti-inflammatory agent.

* * * * *